United States Patent [19]
Klutchko et al.

[11] 4,092,322
[45] May 30, 1978

[54] 1-BENZOXEPINO[4,3-c]PYRIDINES

[75] Inventors: Sylvester Klutchko, Hackettstown; Max von Strandtmann, Rockaway, both of N.J.

[73] Assignee: Warner-Lambert Company, Morris Plains, N.J.

[21] Appl. No.: 768,258

[22] Filed: Feb. 14, 1977

[51] Int. Cl.² .................................. C07D 491/04
[52] U.S. Cl. ......................... 260/294.9; 260/295 T; 260/296 H; 424/256
[58] Field of Search ............ 260/297 T, 295 T, 294.9

[56] References Cited
PUBLICATIONS
Katsujiro et al., Chem. Abstracts, vol. 83 (3), item No. 28,301m, Jul. 21, 1975.

*Primary Examiner*—Alan L. Rotman
*Attorney, Agent, or Firm*—Albert H. Graddis; Frank S. Chow

[57] ABSTRACT

The present invention is concerned with 11-oxo-1-benzoxepino[4,3-c]pyridines of Formula I:

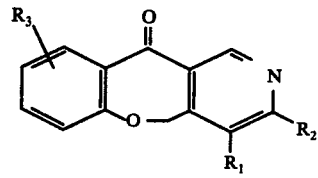

wherein $R_1$ and $R_2$ may be hydrogen, lower alkyl, cyano, carboxamido, carboxy, ethoxycarbonyl or tetrazolyl and $R_3$ may be hydrogen, lower alkyl, halogen, hydroxy or lower alkoxy.

These compounds are indicated in the management of allergic conditions such as bronchial asthma, hay fever and the like.

3 Claims, No Drawings

1-BENZOXEPINO[4,3-c]PYRIDINES

The present invention is concerned with 11-oxo-1-benzoxepino[4,3-c]pyridines of Formula I:

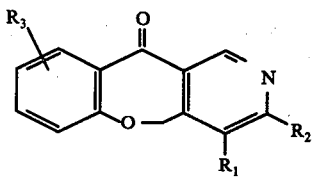

wherein $R_1$ and $R_2$ may be hydrogen, lower alkyl, cyano, carboxamido, carboxy, ethoxycarbonyl or tetrazolyl and $R_3$ may be hydrogen, lower alkyl, halogen, hydroxy or lower alkoxy.

In the above definition for $R_1$, $R_2$ and $R_3$, lower alkyl and the lower alkyl portion of lower alkoxy are meant to have 1-6 carbon atoms as exemplified by such groups as methyl, ethyl, propyl, isopropyl, butyl, isobutyl and so on.

Included among the scope of the present invention are pharmaceutical dosage forms comprising as an active ingredient the above compound.

Also included within the present invention are novel processes for the production of Compound I.

The above compounds exhibit the properties of preventing allergic manifestations, for example, in tests conducted according to the procedures described by I. Mota, Life Sciences, 7: 465 (1963) and Z. Ovary and O. Bier, Proc. Soc. Exptl. Biol. Med., 81: 584 (1952), these compounds exhibit the prevention of allergic manifestations in rats at a dose of about 2 mg/kg orally.

The compounds of the present invention are indicated in the management of allergic manifestations such as bronchial asthma, hay fever and the like. Generally speaking, the compounds are administered orally at a dose of about 2 mg per kg body weight, up to three times daily. This dosage regimen may be varied depending upon the age, sex and weight of the patient being treated by methods well-known to the healing arts. As with any management of allergic conditions, the precise dosage level must also be titrated and individualized.

In order to administer these compounds, they are formulated with inert diluants such as lactose and compounded into dosage forms such as tablets, by methods well-known in pharmaceutical technology.

According to the present invention, the above Compound I is obtained by treating a compound of structural formula II:

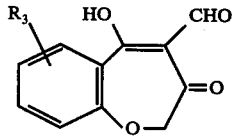

with 3-aminocrotononitrile under reflux conditions in a suitable solvent such as a lower molecular weight alcohol, typically ethyl alcohol. The compound obtained has the following structural formula:

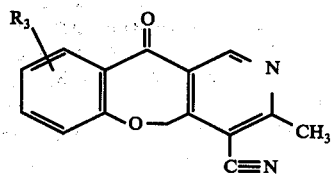

Compound III, having the cyano group, can be converted to other compounds of this invention by methods well-known in the art. For example, acid hydrolysis yields those compounds of the invention in which R is carboxy or converted to tetrazolyl with sodium azide.

Starting Compound II is prepared in accordance with the procedure set out in U.S. Pat. No. 3,991,082, whereas 3-aminocrotononitrile is a known compound available from commercial sources such as Aldrich Chemical Company.

In order to illustrate the practice of the present invention, the following examples are included. In the examples, temperatures are in degrees Centigrade.

EXAMPLE 1

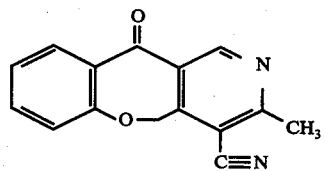

5,11-Dihydro-3-methyl-11-oxo-1-benzoxepino[4,3-c]pyridine-4-carbonitrile.

A solution of 8.16 g (0.04 mole) of 2,3-dihydro-5-hydroxy-3-oxo-1-benzoxepin-4-carboxaldehyde, 4.92 g (0.06 mole) of 3-aminocrotononitrile and 50 ml of absolute ethanol was maintained at reflux for 10 min. and cooled. The separated crystals were filtered, washed with 10 ml ethanol and dried, wt. 5.2 g (52%); mp 124°–126°. Recrystallization was effected by dissolution in 75 ml of 50% dichloromethane-ethanol and removal, by distillation, of most of the dichloromethane. The pure product separated as tan crystals; wt. 2.9 g (29%), mp 126°–128°.

Anal. Calcd. for $C_{15}H_{10}N_2O_2$: C, 71.99; H, 4.03; N, 11.20. Found: C, 71.85; H, 4.10; N, 11.22.

EXAMPLE 2

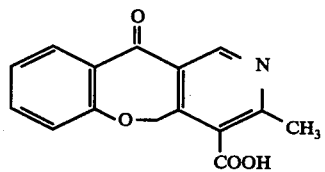

5,11-Dihydro-3-methyl-11-oxo-1-benzoxepino[4,3-c]pyridine-4-carboxylic acid.

A quantity of 7.5 g (0.03 mole) of 5,11dihydro-3-methyl-11-oxo-1-benzoxepino[4,3-c]pyridine-4-carbonitrile was dissolved in 100 ml of 50% sulfuric acid. The solution was heated at 140°–145° for one-half hour and diluted with 400 ml of ice water. The separated crystals were filtered, washed well with water and dried; wt. 6.2 g. Addition of 40% potassium hydroxide to pH ca. 3 precipitated a second crop of the same material (via tlc); wt. 1.1 g. The combined crude products were dissolved in 200 ml of 40% sodium bicarbonate. The solution was charcoaled, filtered and acidified with conc. hydrochloric to pH 4 to precipitate product; wt. 5.0 g (62%); mp 216°–218°. Recrystallization from methanol gave pure product with the same melting point.

Anal. Calcd. for $C_{15}H_{11}NO_4$: C, 66.91; H, 4.12; N, 5.20. Found: C, 66.88; H, 4.25; N, 5.13.

EXAMPLE 3

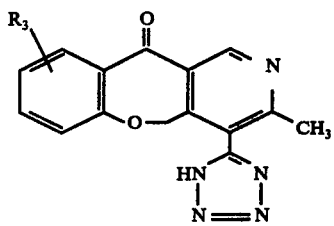

3-Methyl-4-(1H-tetrazol-5-yl)-1-benzoxepino[4,3-c]pyridin-11(5H)-one.

To a stirred mixture of 2.5 g (0.01 mole) of 5,11-dihydro-3-methyl-11-oxo-1-benzoxepino[4,3-c]pyridine-4-carbonitrile, 1.95 g (0.03 mole) of sodium azide and 50 ml of tetrahydrofuran, added, under nitrogen and slowly, 1.5 g of aluminum chloride. The mixture was stirred for 1 hour at reflux, cooled and treated with another 1.5 g of aluminum chloride. The mixture was maintained at reflux for 48 hours and cautiously added to 150 ml of ice water. Conc. hydrochloric acid (5 ml) was added and the crude solid was filtered. This was stirred with 200 ml of 3% sodium bicarbonate and the insolubles were filtered. The filtrate was acidified with conc. hydrochloric acid to pH 3. The separated white solid was filtered, washed with water and dried, wt. 0.15 grams (5%); mp 180°–182°. Recrystallization from methanol gave pure product; mp 183°–185°.

Anal. Calcd. for $C_{15}H_{11}N_5O_2$: C, 61.43; H, 3.78; N, 23.88. Found: C, 61.26; H, 3.94; N, 23.79.

We claim:
1. A compound of the formula:

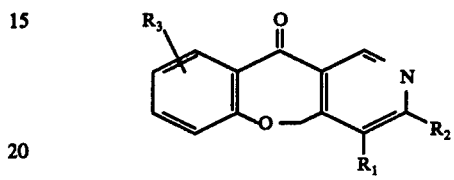

wherein $R_1$ may be hydrogen or lower alkyl, $R_2$ may be cyano, carboxamido, carboxy or ethoxycarbonyl, and $R_3$ may be hydrogen, lower alkyl, halogen, hydroxy or lower alkoxy.

2. A compound according to claim 1 which is 5,11-dihydro-3-methyl-11-oxo-1-benzoxepino[4,3-c]pyridine-4carbonitrile.

3. A compound according to claim 1 which is 5,11-dihydro-3-methyl-11-oxo-1-benzoxepino[4,3-c]pyridine-4-carboxylic acid.

* * * * *